United States Patent
Wu et al.

(10) Patent No.: US 11,219,972 B2
(45) Date of Patent: Jan. 11, 2022

(54) SOLDERING PROCESS METHOD

(71) Applicant: DELTA ELECTRONICS, INC., Taoyuan (TW)

(72) Inventors: Shu-Han Wu, Taoyuan (TW); Hung-Wen Chen, Taoyuan (TW); Qi-Ming Huang, Taoyuan (TW); Yang-Hao Chou, Taoyuan (TW); Yun-Chung Sun, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 294 days.

(21) Appl. No.: 16/106,007

(22) Filed: Aug. 21, 2018

(65) Prior Publication Data

US 2019/0291217 A1 Sep. 26, 2019

(30) Foreign Application Priority Data

Mar. 23, 2018 (CN) .......................... 201810245525.X

(51) Int. Cl.
*B23K 31/00* (2006.01)
*G16C 20/00* (2019.01)
*B23K 31/12* (2006.01)
*B23K 26/20* (2014.01)
*G16C 20/70* (2019.01)

(52) U.S. Cl.
CPC .............. *B23K 31/12* (2013.01); *B23K 26/20* (2013.01); *G16C 20/70* (2019.02)

(58) Field of Classification Search
None
See application file for complete search history.

(56) References Cited

U.S. PATENT DOCUMENTS

| | | | | | |
|---|---|---|---|---|---|
| 5,439,160 | A | * | 8/1995 | Marcantonio | B23K 1/008 228/102 |
| 6,043,454 | A | * | 3/2000 | Sheffer | B23K 26/04 219/121.63 |
| 6,072,150 | A | * | 6/2000 | Sheffer | B23K 26/04 219/121.76 |

(Continued)

FOREIGN PATENT DOCUMENTS

| | | |
|---|---|---|
| CN | 102183545 A | 9/2011 |
| CN | 105414817 A | 3/2016 |

(Continued)

OTHER PUBLICATIONS

Tsai et al., "Development of Diagnosis System for Reflow Soldering using Neural Networks and Support Vector Regression", International Journal of Industrial Engineering, vol. 21, issue 1, p. 19-33, 2014, (Year: 2014).*

(Continued)

*Primary Examiner* — Devang R Patel
(74) *Attorney, Agent, or Firm* — CKC & Partners Co., LLC

(57) ABSTRACT

A soldering process method includes the following steps. A temperature profile of generating a solder structure is measured. A final product of the solder structure is tested and recorded. A machine learning method is used to repeatedly compare and analyze a relationship between a plurality of the temperature profiles of the solder structure and a corresponding final product of the solder structure so as to find an optimal temperature profile model in accordance with quality control requirements.

4 Claims, 5 Drawing Sheets

(56) References Cited

U.S. PATENT DOCUMENTS

| | | | | |
|---|---|---|---|---|
| 6,138,893 A * | 10/2000 | Caletka | ................ | B23K 3/08 228/102 |
| 6,204,490 B1 * | 3/2001 | Soga | ................ | B23K 1/0056 219/678 |
| 6,560,514 B1 * | 5/2003 | Schultz | ................ | G05B 13/024 700/209 |
| 6,797,926 B2 * | 9/2004 | Yamauchi | ................ | B23K 3/087 219/444.1 |
| 6,799,712 B1 * | 10/2004 | Austen | ................ | B23K 1/008 219/413 |
| 8,123,110 B2 * | 2/2012 | Berger | ................ | B23K 1/19 228/233.2 |
| 8,299,393 B2 * | 10/2012 | Kelly | ................ | B23K 1/0016 219/121.63 |
| 2008/0177412 A1 * | 7/2008 | Yamaguchi | ................ | B23K 1/008 700/114 |
| 2009/0206145 A1 * | 8/2009 | Tamori | ................ | B23K 1/008 228/15.1 |
| 2010/0206854 A1 * | 8/2010 | Nakai | ................ | B23K 1/0056 219/121.6 |
| 2016/0031044 A1 * | 2/2016 | Marino | ................ | H05K 3/225 228/102 |
| 2018/0015560 A1 * | 1/2018 | Narayanan | ................ | B23K 26/38 |

FOREIGN PATENT DOCUMENTS

| | | | |
|---|---|---|---|
| CN | 106416455 | A | 2/2017 |
| CN | 106501272 | A | 3/2017 |
| TW | 453145 | B | 9/2001 |
| TW | 200308070 | A | 12/2003 |
| TW | I590905 | B | 7/2017 |

OTHER PUBLICATIONS

Tsung-Nan Tsai et al., "Development of a Closed-Loop Reflow Soldering Process Diagnosis System by Integrating Neural Network and Support Vector Regression", International Journal of Industrial Engineering, 21(1), 25-39, 2014.

* cited by examiner

SOLDERING PROCESS METHOD

RELATED APPLICATIONS

This application claims priority to China Application Serial Number 201810245525.X, filed Mar. 23, 2018, which are herein incorporated by reference.

BACKGROUND

Field of Invention

The present disclosure relates to a soldering process method, and more particularly to a soldering quality control method.

Description of Related Art

Soldering is a necessary process step in the production processes of electronic products, whether it is used for a DIP component or a SMD component that the soldering must be used to attach the component to the circuit board. The quality of the solder joint affects the product performance and life, and the operational quality of the soldering process is highly valued. In the current production line, the methods for solder inspection include: In-Circuit Test (ICT test), X-ray test, and Automated Optical Inspection (AOI test). However, when these inspection tests are performed, each test has its associated limitations or disadvantages.

The ICT test is an electrical test. By forming designated test points on the circuit board in advance, a probe and an electrical detection device are used to detect the circuit condition of the components thereon and find out whether there is an open circuit or a short circuit. As for equipment cost considerations, ICT testing equipment and fixtures are expensive, and only production lines of enough production can afford the cost. The X-ray test is a penetration-type and non-destructive inspection. It can perform internal image inspection on solder joints, including whether there are bubbles, solder bridges, insufficient solder, etc., but it cannot effectively detect empty solder or cold welding. The AOI inspection is an optical image inspection. It can only detect an outer appearance of the solder joint, and cannot detect an internal problems or welding interface issue of the solder joint. In addition to 2D images, 3D complex image or stereo image technology is also used to inspect the solder joint, but the results are still not significant. It is difficult to judge whether the solder joint meets a quality control requirement merely from an outer appearance inspection, and is therefore hard to adjust the AOI inspection parameters to improve false judge rate.

SUMMARY

In one or more embodiments, a soldering process method includes steps of: measuring a temperature profile of generating a solder structure; testing and recording a final product of the solder structure; and using a machine learning method to repeatedly compare and analyze a relationship between a plurality of the temperature profiles of the solder structure and a corresponding final product of the solder structure so as to find an optimal temperature profile model. Thus, the final product of the solder structure meets a quality control requirement.

In one or more embodiments, a soldering process method includes steps of: measuring a temperature profile of generating a solder structure; testing and recording a final product of the solder structure; and using a machine learning method to repeatedly compare and analyze a relationship between a plurality of the temperature profiles the solder structure and a corresponding final product of the solder structure so as to find a classified temperature profile model that is judged to be a disqualified condition which is inconsistent with quality control requirements.

In one or more embodiments, the soldering process method further includes a step of measuring the temperature profile of generating the solder structure by using a non-contact method.

In one or more embodiments, the temperature profile of generating the solder structure includes a temperature profile of a processing, such as heating, solder feeding, cooling or any combinations thereof.

In one or more embodiments, the machine learning method includes supervised learning.

In one or more embodiments, the soldering process method further includes a step of heating another solder structure according to the optimal temperature profile model.

In one or more embodiments, the soldering process method further includes a step of heating the solder structure.

In one or more embodiments, the soldering process method further includes a step of using a laser beam or a soldering iron to heat the solder structure.

In one or more embodiments, the soldering process method further includes a step of using an infrared temperature device to measure the temperature profile of generating the solder structure.

In one or more embodiments, the disqualified condition includes tin explosion, empty solder (solder skipping), cold welding or no solder.

In one or more embodiments, the soldering process method further includes a step of using a classified temperature profile model for tin explosion to determine whether solder structures to be tested have a tin explosion condition.

In one or more embodiments, the soldering process method further includes a step of using a classified temperature profile model for empty solder to determine whether solder structures to be tested have an empty solder condition.

In one or more embodiments, the soldering process method further includes a step of using a classified temperature profile model for cold welding to determine whether solder structures to be tested have a cold welding condition.

In one or more embodiments, the soldering process method further includes a step of using a classified temperature profile model for no solder to determine whether solder structures to be tested have a no solder condition.

In sum, the present invention utilizes machine learning as a method of generating a temperature profile model, similar applications of the machine learning model can increase soldering experience into a knowledge base, and the solder structure can be analyzed according to the judgment rules established by the knowledge base. Compared with traditional solder testing methods, the present invention utilizes the most important factor "temperature" of the soldering process as a quality control factor. From heating, solder feed, to cooling, the temperature profile at each phase or stage of the soldering process is recorded and valued, and the temperature change caused by the actual phenomenon is also analyzed, which is better than the traditional method judging only from the final result.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
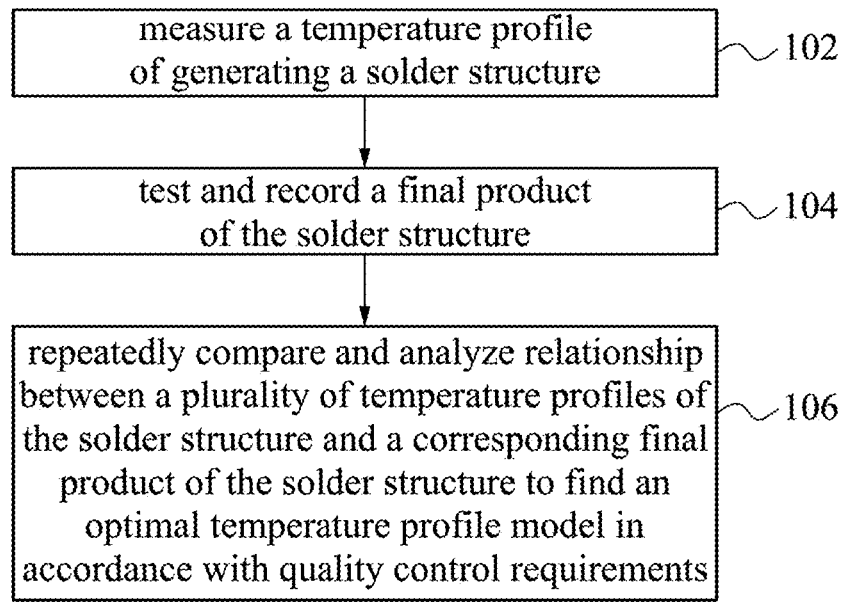
FIG. 1 illustrates a machine learning training method for soldering process according to one embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

The present invention provides a solder manufacturing method that uses a temperature profile to determine solder quality and improve solder quality. The soldering process method includes a pre-training method and a subsequent inspection or soldering improvement method.

FIG. 1 illustrates a machine learning training method 100 for soldering process according to one embodiment of the present disclosure. The training method 100 is a machine learning training method, which utilizes, for example, supervised learning to find a desired temperature profile model for the soldering process.

In step 102, a temperature profile of generating a solder structure is measured. The temperature-measuring method may be a contact type or a non-contact type measuring temperature mode. In the production process, the non-contact type measuring temperature mode has the advantages of not affecting the existing soldering process. The non-contact measurement temperature method may be, for example, an infrared temperature measurement, but is not limited thereto The temperature profile of generating a solder structure is, for example, a temperature profile for a process, such as heating, solder feeding, and/or cooling.

In step 104, a final product of the solder structure is tested and recorded. The method for testing the final product of the solder structure may be aforementioned ICT test, X-ray test, AOI test or solder structure micro-section inspection, etc.

In step 106, a machine learning method is used to repeatedly compare and analyze a relationship between a plurality of the temperature profiles of the solder structure and a corresponding final product of the solder structure so as to find an optimal temperature profile model in accordance with quality control requirements, i.e., the final product of the solder structure meets a quality control requirement. A regression model, for example, may be used to compare and analyze the relationship between a plurality of the temperature profiles of the solder structure and the corresponding final product of the solder structure so as to obtain the optimal temperature profile model. In particular, the training method 100 may be utilized to measure the temperature profile of generating solder structure in the solder production line, and subsequently test and record the final products of the solder structures. The relationships between the temperature profiles of the solder structures and the corresponding final product of the solder structures are compared and analyzed by machine learning so as to find out an optimal temperature profile model for the final product of the solder structure in accordance with the quality control requirements.

Figure 2:
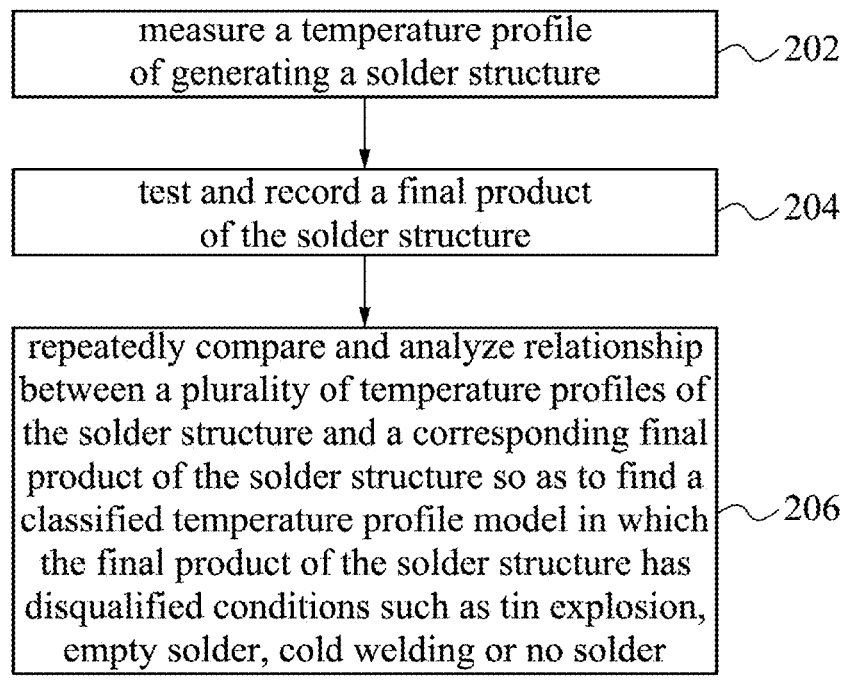
FIG. 2 illustrates a machine learning training method for soldering process according to another embodiment of the present disclosure.

In an actual soldering production line, there may be a few final products of the solder structure that are inconsistent with the quality control requirements, i.e., has a disqualified condition, and the similar training method 100 still needs to be performed. Referring to FIG. 2, it shows another machine learning training method 200 for soldering process according to another embodiment of the present disclosure.

In step 202, a temperature profile of generating a solder structure is measured. The temperature-measuring method may be a contact or non-contact measuring method. In the production process, the non-contact measuring method has the advantage of not affecting the existing soldering process. The non-contact measuring method may be conducted by an infrared temperature-measuring device, for example, but being not limited thereto. The temperature profile of generating a solder structure is, for example, a temperature profile of a process, such as heating, solder feeding, and/or cooling.

In step 204, a final product of the solder structure is tested and recorded. The method for testing the final product of the solder structure may be aforementioned ICT test, X-ray test, AOI test or solder structure micro-section inspection, etc. It should be noted that X-RAY test, AOI test, and solder structure micro-section inspection are image-inspection test, but the ICT test are electrical tests to determine whether the solder structure is short-circuited, broken circuit or open circuit.

In step 206, a machine learning method is used to repeatedly analyze a relationship between the temperature profile of the solder structure and a corresponding final product of the solder structure so as to find a classified temperature profile model in which the final product of the solder structure has a disqualified condition which is inconsistent with the quality control requirements. In particular, the training method 200 may be utilized to measure the temperature profile of generating solder structure in the solder production line, and subsequently test and record the final products of the solder structures that have a disqualified condition inconsistent with the quality control requirements. The relationships between the temperature profiles of the solder structures and the corresponding final products of the solder structures are compared and analyzed by machine learning so as to find out respective classified temperature profile models for various final products of the solder structures that have a disqualified condition inconsistent with the quality control requirements.

The above-mentioned disqualified conditions for solder structures include a state of tin explosion, empty solder (solder skipping), cold welding or no solder of the solder structure, but not limited thereto. The "tin explosion" refers to the situation where the solder structure is "exploded" and sputtered during the soldering process. The "empty solder" refers to the situation where the solder structure appears to meet the requirements for quality control from the outer appearance, but an inner core of the solder structure is hollow. The "cold soldering" refers to solder structure defects caused by accumulating not enough heat to reach the solder melting temperature due to heat dissipation during soldering process. The "no solder" means the solder is not present in the place it should be. The quality defects may be caused by running out the tin wire, the jamming of the tin feeding mechanism, or the solder paste not applied properly.

The final product of the solder structure obtained by the above-described training method 100 meets the optimal temperature profile model required by the quality control. The optimal temperature profile model is, for example, a mathematical polynomial or segment polynomial to match the temperature profile of an optimal (or well qualified) solder structure. The optimal temperature profile model may serve as a standard in the follow-up actual production, that is, a solder structure in actual production is heated according to the optimal temperature profile model. In an embodiment, the solder structure may be heated by using a laser beam or a soldering iron.

For example, if a temperature profile of a certain stage deviates from the optimum temperature profile model, in the process of heating the solder structure with the laser light, the beam diameter or the laser power can be adjusted instantly to correct the temperature profile of the solder structure. If the soldering iron is used to heat the soldering structure, the temperature profile of the soldering structure can be corrected by adjusting the power supply wattage or the shape or size of the soldering iron tip so as to reduce the defective rate or the rework rate.

Figure 3:
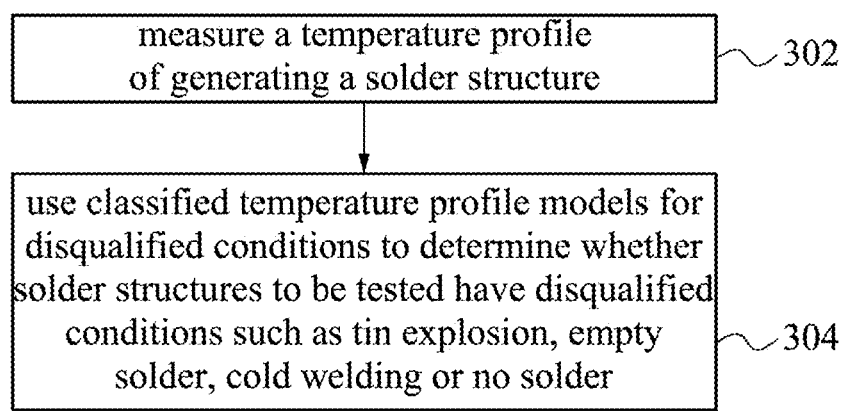
FIG. 3 illustrates a solder structure defect detection method for soldering process according to one embodiment of the present disclosure.

The classified temperature profile model of various conditions of the final product of the solder structure obtained by the training method 200 is used to predict or determine the type of the bad solder structure, so as to reduce the quality control cost and facilitate the arrangement of the correct rework method as illustrated in defect detection method 300 of FIG. 3.

FIG. 3 illustrates a solder structure defect detection method 300 for soldering process according to one embodiment of the present disclosure.

In step 302, a temperature profile of generating a solder structure is measured. The temperature-measuring method may be a contact or non-contact measuring method. In the production process, the non-contact measuring method has the advantage of not affecting the existing soldering process. The non-contact measuring method may be conducted by an infrared temperature-measuring device, for example, but being not limited thereto. The temperature profile of generating a solder structure is, for example, a temperature profile of a process, such as heating, solder feeding, and/or cooling.

In step 304, the temperature profiles obtained in step 302 are compared with the temperature profiles of various disqualified solder structures to be tested to find the closest associated condition. For example, the disqualified condition includes tin explosion, empty solder, cold welding or no solder. The classified temperature profile models obtained from step 206 for respective disqualified conditions would be utilized one by one to determine which classified temperature profile model can be properly applied to determine whether solder structures to be tested have a condition of tin explosion, empty solder (solder skipping), cold welding or no solder.

Figure 4:
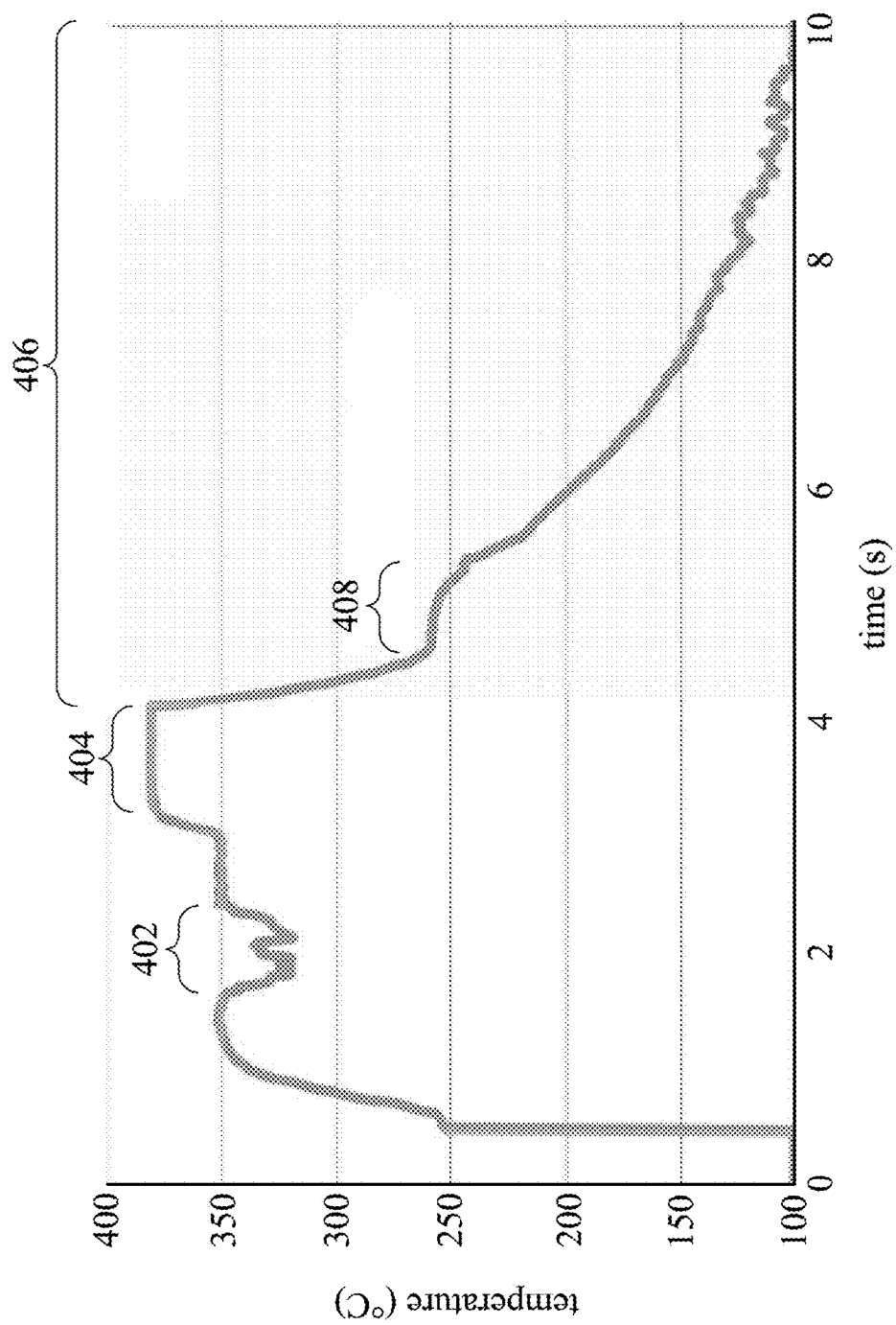
FIG. 4 illustrates an optimal temperature profile model for a final product of a soldering structure which meets a quality control requirement according to one embodiment of the present disclosure.

FIG. 4 illustrates an optimal temperature profile model for a final product of a soldering structure, which meets a quality control requirement according to one embodiment of the present disclosure.

The optimum temperature profile model is a temperature profile model obtained by a process of heating a solder structure by a laser. This temperature profile model includes a temperature profile of tin (solder) feeding phase 402, a temperature profile of tin (solder) wetting phase 404, and a temperature profile of tin (solder) curing transition phase 408. The tin (solder) wetting phase 404 can also be referred to as a tin (solder) heat absorbing or active phase. This optimum temperature profile model is only an example for the optimum temperature profile model of the laser heating solder process. It does not represent the optimum temperature profile model of all solder processes, nor is it used to limit the model of the optimal temperature profile. For example, the tin (solder) feeding phase 402 may not be suitable for other soldering processes, i.e., a soldering process without a tin (solder) feeding phase would not have a temperature profile model with a short temperature drop during the tin (solder) feeding phase 402.

Figure 5:
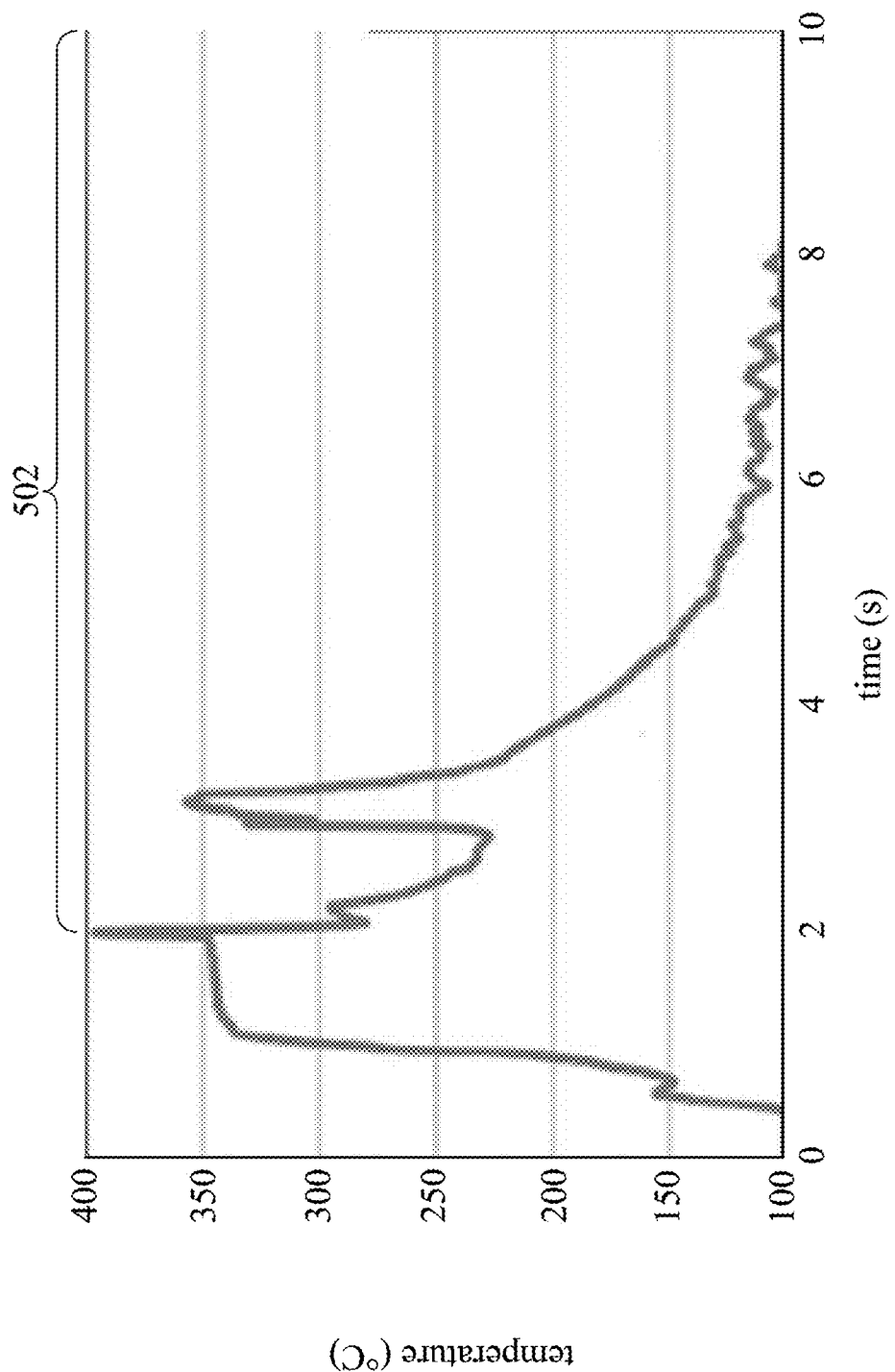
FIG. 5 illustrates a classified temperature profile model in which solder structures to be tested have a disqualified condition of "no solder" according to one embodiment of the present disclosure.

FIG. 5 illustrates a classified temperature profile model in which the final product of the solder structure has a disqualified condition of "no solder" according to one embodiment of the present disclosure.

The "no solder" indicates that the defect is formed because the solder is not present in the place it should be. The major feature of the "no solder" classified temperature profile model is "no obvious curing transition phase." Specifically, when the cooling stage 406 of FIG. 4 is compared with the cooling stage 502 of FIG. 5, the cooling stage 502 does not have a temperature profile model similar to the curing transition phase 408 of FIG. 4, i.e., approximately the same temperature is maintained briefly during the curing transition phase 408.

Figure 6:
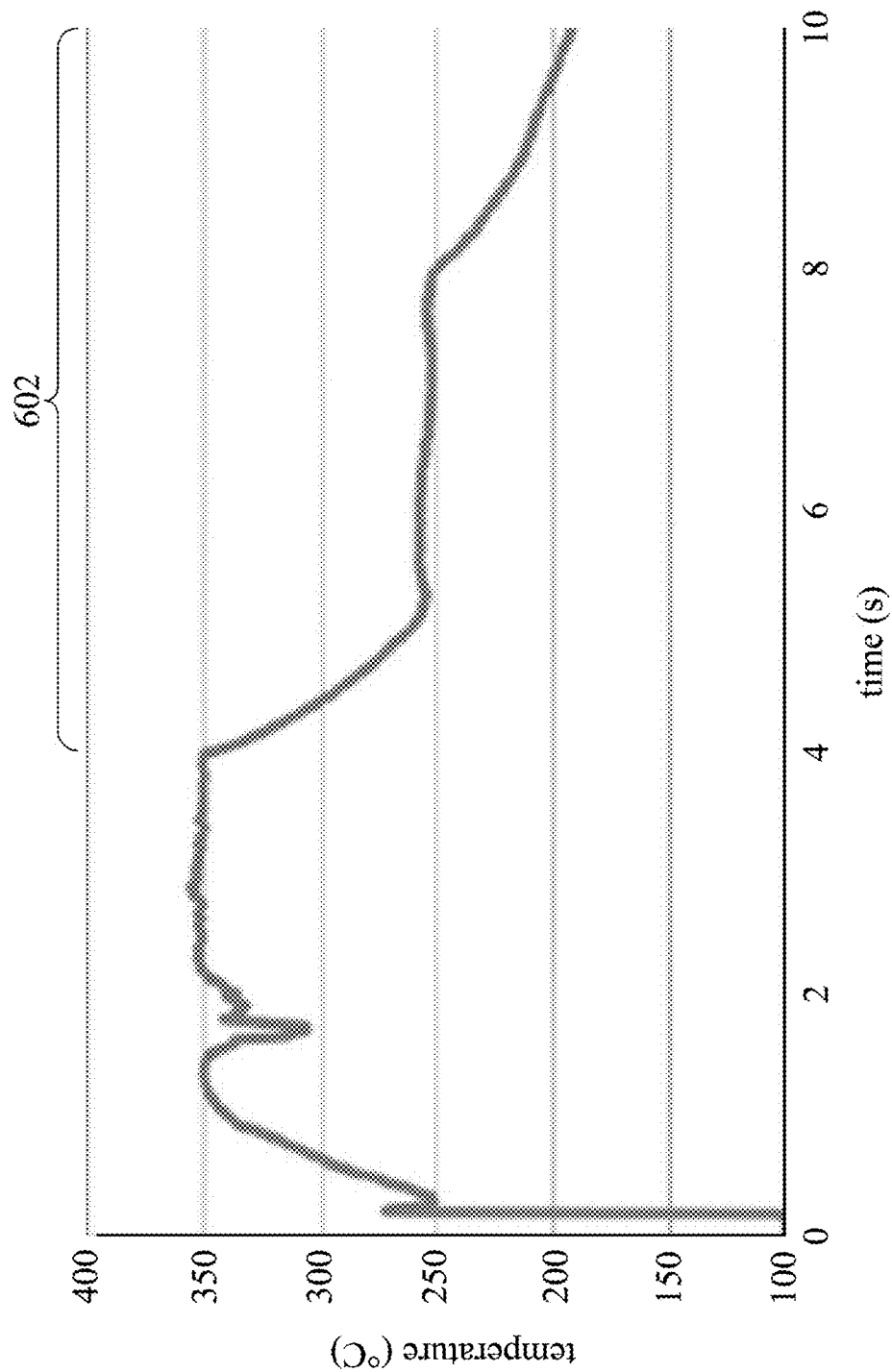
FIG. 6 illustrates a classified temperature profile model in which the final product of the solder structure has a disqualified condition of "empty solder" according to one embodiment of the present disclosure.

FIG. 6 illustrates a classified temperature profile model in which the final product of the solder structure has a disqualified condition of "empty solder" according to one embodiment of the present disclosure. The "empty solder" refers to the situation where the solder structure appears to meet the requirements of quality control from the outer appearance, but an inner core of the solder structure is hollow. The major feature of the classified temperature profile model for "empty solder" is that the temperature of the cooling stage decreases slowly due to slow heat releasing. Specifically, when the cooling stage 406 of FIG. 4 is compared with the cooling stage 602 of FIG. 6, the cooling stage 602 decreases slower than the cooling stage 406.

Although Figures herein only shows the temperature profiles of the disqualified conditions such as "no solder" and "empty solder", the classified temperature profile models for "tin (solder) explosion" and "cold welding" can also be obtained by the above-mentioned machine learning training method.

In sum, the present invention utilizes machine learning as a method of generating a temperature profile model, similar applications of the machine learning model can add soldering experience into a knowledge base, and the solder structure can be analyzed according to the judgment rules established by the knowledge base. Compared with traditional solder testing methods, the present invention utilizes the most important factor "temperature" of the soldering process as a quality control factor. From heating, tin input, to cooling, the temperature profile at each phase or stage of the soldering process is recorded and valued, and the temperature change caused by the actual phenomenon is also analyzed, which is better than the traditional method judging only from the final product.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A soldering process method, comprising steps of:
   using a laser beam to heat a solder structure;
   measuring a temperature profile of generating the solder structure;
   testing and recording a final product of the solder structure; and
   using a machine learning method to repeatedly compare and analyze a relationship between a plurality of the temperature profiles of the solder structure and a corresponding final product of the solder structure so as to find an optimal temperature profile model of the final product of the solder structure in accordance with quality control requirements, wherein the optimal temperature profile model comprises a temperature profile of a solder feeding phase, a temperature profile of a solder heat absorbing and wetting phase, and a temperature profile of a cooling stage, wherein the temperature profile of the cooling stage has a decreasing temperature segment of a solder curing transition phase,
   the temperature profile of the solder feeding phase lasts at least 0.5 second and has a decreasing temperature segment, an increasing temperature segment and a wavy temperature segment connected between the decreasing temperature segment and the increasing temperature segment, and the temperature profile of the solder heat absorbing and wetting phase has a temperature segment that stays at the same temperature for at least 0.5 second.

2. The method of claim 1, further comprising a step of:
   measuring the temperature profile of generating the solder structure by using a non-contact method.

3. The method of claim 1, wherein the machine learning method comprises supervised learning.

4. The method of claim 1, further comprising a step of:
   heating another solder structure according to the optimal temperature profile model.

* * * * *